(12) United States Patent
Hudson (10) Patent No.: US 7,711,580 B1
(45) Date of Patent: May 4, 2010

(54) SYSTEM AND METHOD FOR MATCHING PATIENTS WITH CLINICAL TRIALS

(75) Inventor: Courtney Hudson, New York, NY (US)

(73) Assignee: Emergingmed.com, New York, NY (US)

( * ) Notice: Subject to any disclaimer, the term of this patent is extended or adjusted under 35 U.S.C. 154(b) by 959 days.

(21) Appl. No.: 09/699,372

(22) Filed: Oct. 31, 2000

(51) Int. Cl.
- G06F 19/00 (2006.01)
- G06Q 50/00 (2006.01)
- G09B 3/00 (2006.01)
- A61B 5/00 (2006.01)

(52) U.S. Cl. .............................. 705/3; 705/2; 434/322; 600/300

(58) Field of Classification Search ................ 705/2–3; 600/300
See application file for complete search history.

(56) References Cited

U.S. PATENT DOCUMENTS

| | | | | |
|---|---|---|---|---|
| 5,572,421 | A | * | 11/1996 | Altman et al. ................. 705/3 |
| 5,734,883 | A | | 3/1998 | Umen et al. |
| 5,898,586 | A | | 4/1999 | Jeatran et al. |
| 5,991,731 | A | * | 11/1999 | Colon et al. .................... 705/3 |
| 6,081,786 | A | | 6/2000 | Barry et al. |
| 6,108,665 | A | | 8/2000 | Bair ........................... 707/104 |
| 6,151,581 | A | * | 11/2000 | Kraftson et al. ................ 705/3 |
| 6,839,678 | B1 | * | 1/2005 | Schmidt et al. ................ 705/3 |
| 7,054,823 | B1 | * | 5/2006 | Briegs et al. .................... 705/2 |
| 7,251,609 | B1 | * | 7/2007 | McAlindon et al. ............ 705/3 |
| 2001/0051882 | A1 | * | 12/2001 | Murphy et al. ................. 705/3 |
| 2002/0002474 | A1 | * | 1/2002 | Michelson et al. ............. 705/3 |
| 2002/0035486 | A1 | * | 3/2002 | Huyn et al. ..................... 705/3 |
| 2002/0099570 | A1 | * | 7/2002 | Knight ........................... 705/2 |
| 2006/0104941 | A1 | * | 5/2006 | Ridker et al. ............. 424/78.12 |

FOREIGN PATENT DOCUMENTS

| | | | |
|---|---|---|---|
| EP | 936566 | A2 * | 8/1999 |
| WO | 98/39720 | | 9/1998 |
| WO | 98/49647 | | 11/1998 |
| WO | WO 01/55942 | A1 | 1/2001 |

OTHER PUBLICATIONS

Anonymous. "How to Keep Rolling in Enrollment." R&D Directions. Mar. 1998, vol. 4, No. 2, pp. 10-11.*

(Continued)

Primary Examiner—C. Luke Gilligan
Assistant Examiner—Rachel L Porter
(74) Attorney, Agent, or Firm—Hanify & King, P.C.

(57) ABSTRACT

A system and method for matching patients with clinical trials and particular trial sites, prequalifying patients for clinical trials and trial sites, and providing information to patients to allow them to inform themselves about available clinical trials and trial sites. The method comprises receiving patient profile information for a patient at a server connected to a computer network, the patient profile information submitted by a user at a terminal connected to the network, comparing the patient profile information with acceptance criteria for clinical trials stored in a database, the comparison performed by the server, determining whether the patient prequalifies for any of the clinical trials, and notifying the user and the trial site whether the patient has prequalified for any clinical trials.

32 Claims, 3 Drawing Sheets

OTHER PUBLICATIONS

Centerwatch Website printout packet, printed Nov. 12, 2002, archived Dec. 1998, 13 pages.*
Anonymous, "Pharmaceutical Industry Embraces Clinmark Dotcom," Jul. 6, 1998, Business Wire, 2 pages.*
U.S. Appl. No. 60/178,634, Michelson et al.*
Machlis, Sharon; "Web Links Cancer Patients to Drug Trials," Oct. 14, 1998, Cnn.com, 4 pages.*
Machlis,Sharon "Web Links Cancer Patients to Drug Trials," Oct. 14, 1998, www. CNN.com (From Computerworld)—2 pages.*
Soetikno, Roy et al , "Quality of Life Research on the Internet: Feasibility and Potential Biases in Patients with Ulcerative Colitis." Nov/ Dec. 1997, Journal of the American Medical Informatics Association; vol. 4, No. 6, pp. 426-435.*
XP-002065364—Article: Chester King, Robert M. Strong, Larry Goldstein, Medus/A: Distributing Database Management for Medical Research: Health Systems Project, Harvard School of Public Health, published Sep. 20, 1982 pp. 635-642.
Abstract, Dialog file 16 (Gale group PROMT(R) No. 6439375, drkooop.com & Quintiles Launch Service to Recruit Clinical Trial Patients on the Internet, PR Newswire, 3 pages (Jun. 1999).
McCray, Alexa T. "A National resource for information on clinical trials," National Forum, vol. 79, No. 3, pp. 19-21, (Sep. 1999).
Ukens, Carol, "CenterWatch is hub of clinical trials Web sites," Drug Topics, vol. 143, No. 8, pp. 112, (Apr. 1999).
Zoeller, Janice, "Surfing for complementary info." American Druggist, vol. 216, No. 9, pp. 15, (Sep. 1999).
Baldwin, Gary, "System makes it easier to link patients to clinical trials," American Medical News, Nov. 16, 1998, vol. 41, No. 53, pp. 25.
Anonymous, TVisions Wins Top Web Externet Award; recognized for Creative Life-Saving Site, Business Wire, Jul. 1, 1999, No. 42844318, p. 1.
Mellen, Sue, "TVisions builds a site for onconology researches and their clinical trials", Mass High Tech, Jul. 26, 1999, vol. 17, No. 30, p. 10.
Anonymous, "Object Products, Inc. to Demonstrate Clinical Trials Patient Recruitment Solution at HIMSS", Business Wire, Jan. 26, 1999, No. 38453864, p. 1.
Larkin, Marilynn, "Where to find clinical trials on the Web", The Lancet, Apr. 11, 1998, vol. 351, No. 9109, p. 1140.
Anonymous, "Pharmaceutical Industry Embraces Clinmark Dotcom; Success Stories Abound for the Industry's Largest Internet-Based Investigator Database", Business Wire, Jul. 6, 1998, 2 pages.
Anonymous, "If you'd like to join a clinical trial . . . ", Tufts University Health & Nutrition Letter, Oct. 1998, vol. 16, No. 8, p. 3.

* cited by examiner

SYSTEM AND METHOD FOR MATCHING PATIENTS WITH CLINICAL TRIALS

FIELD OF THE INVENTION

The present invention relates to a system and method for matching patients with clinical trials. More specifically, the present invention relates to a system and method for quickly and efficiently matching patients with clinical trials and clinical trial sites over a computer network.

BACKGROUND OF THE INVENTION

Many companies sponsor clinical trials for new drugs, medical devices, therapies, or treatment programs. Typical clinical trial sponsors include pharmaceutical companies, biotech companies, medical device companies, clinical research organizations (CRO's), and site management organizations (SMO's). Clinical trials are often an important step before obtaining FDA approval for particular drugs.

Patients who have been diagnosed with a disease are often in need of finding appropriate clinical trials for new drugs, medical devices, or treatments to treat their disease. Patients with serious diseases may only have weeks or months to live, and thus the ability to find available clinical trials and information about those trials quickly and efficiently is invaluable. Unfortunately today, there is no effective system for quickly matching patients with clinical trials. Doctors are often not aware of all the clinical trials that are being performed in different geographic regions. Clinical trial sponsors have difficulty finding suitable patients for their trials because there is a lack of up-to-date listings of clinical trials, patients are geographically dispersed, many clinical trials require screening large segments of the population, and patients lack insurance coverage. Additionally, patients seeking on their own to find clinical trials which may help them often suffer from consumer confusion with regard to medical terminology and protocol information, and thus have a difficult time identifying appropriate clinical trials.

Clinical trial sponsors are also hurt by this problem, since the inability to quickly find acceptable patients to enroll in their trials delays development of their new drugs or devices and delays FDA approval. What is needed is a method of quickly and efficiently matching qualifying patients with appropriate clinical trials. What is also needed is a system that can match patient medical profiles and patient characteristics with clinical trial acceptance criteria for a wide range of clinical trials in dispersed geographic areas. What is also needed is a source of comprehensive information about diseases, drugs, medical devices, and clinical trials to provide patients, family, friends and health care professionals the necessary information to make informed decisions about which clinical trials are useful for treating various conditions, and other related information such as risks, benefits, insurance coverage, and other similar information.

SUMMARY OF THE INVENTION

The present invention is a system and method for matching patients with clinical trials and trial sites, prequalifying patients for clinical trials and trial sites, and providing information to patients to allow them to inform themselves about available clinical trials and trial sites. The method of the present invention comprises receiving patient profile information for a patient at a server connected to a computer network such as the Internet. The patient profile information is submitted by a user at a terminal connected to the network. A server compares the patient profile information with acceptance criteria (including geographic location) for clinical trials and trial sites stored in a database. The server determines whether the patient qualifies for any of the clinical trials, and notifies the user whether the patient has prequalified for any clinical trials.

The patient's profile is built by asking the user a series of questions and then creating the patient profile based on the user's responses. The questions can include static and dynamic questions. The user is also asked a series of questions targeted to a specific clinical trial or trial site after determining that the patient meets the preliminary acceptance criteria for the specific clinical trial or trial site. The final determination of whether the user prequalifies is based on the user's response to the targeted questions.

When the user is provided with a question, the user is also provided with a set of answer options. The user responds to the question by choosing one or more of the answer options. Alternatively, the user can type in an answer to the question.

Once the user has prequalified for a clinical trial/trial site, the user is provided with an application. The user fills out the application and can submit the application on-line. The application and the patient's medical profile are sent to the appropriate trial site. The patient's application and medical profile do not include the patient's name, social security number or other identifying information. This protects the patient's privacy. If the patient is accepted by the trial site, the patient is notified and provided with trial site contact information. The patient can contact the trial site to enroll in the clinical trial.

DETAILED DESCRIPTION OF THE INVENTION

The system of the present invention brings patients together with clinical trials by allowing patients, health care professionals, clinical trial sponsors, and clinical trial investigators to access a centralized database. The system matches patient profile information with clinical trial acceptance criteria to determine whether a patient prequalifies for particular trials. Once the system of the present invention determines that a patient prequalifies for a particular clinical trial site, the patient is then placed in contact with the clinical trial site so that the patient can enroll in the clinical trial. The clinical trial site may require that the patient undergo medical testing or answer additional questions before enrollment is permitted. Thus, the system of the present invention performs the process of "prescreening" or "prequalifying."

In a preferred embodiment of the invention, the system resides on a server on the Internet. Users of the system can conveniently access the system over the World Wide Web. Patients and trial sites can access the system by visiting the EmergingMed.com web site.

In addition to matching patients with clinical trials, the server of the present invention also allows patients to search and view information about aspects of various diseases, drugs, medical devices, clinical trials, treatment programs, medical news, research and other similar sources of medical information. Patients who visit the EmergingMed.com web site can get educated on the disease for which they have been diagnosed and the available clinical trials. Health care professionals can also access the EmergingMed.com web site to learn the latest medical information. They can also learn about what various clinical trials are available for that disease, which trials are already closed (i.e. the sponsoring companies are not taking any more patients), and which trials are still open and taking patients.

Clinical trial sponsors include pharmaceutical companies, biotech companies, medical device companies, clinical research organizations (CRO's), and site management organizations (SMO's). The EmergingMed.com web site benefits clinical trial sponsors by allowing them to quickly find, prescreen and recruit suitable patients for their clinical trials. The EmergingMed.com web site thus allows the trial sponsors to accelerate the conduct and completion of their clinical trials in order to obtain FDA approval or demonstrate additional efficiency for particular drugs or devices. By accelerating the conduct and completion of clinical trials, these companies can effectively reduce costs and speed up time to market.

The individual or group of individuals who actually conduct a clinical trial for a sponsor will be referred to herein as an "investigator." The investigator or investigators conduct clinical trials at clinical trial sites. For example, a drug company is interested in conducting trials for a new drug which it has just developed for fighting cancer. A doctor is conducting a clinical trial for the drug company at New York Hospital in New York. The drug company is the clinical trial sponsor. The doctor is the investigator. New York Hospital is the clinical trial site.

Figure 1:
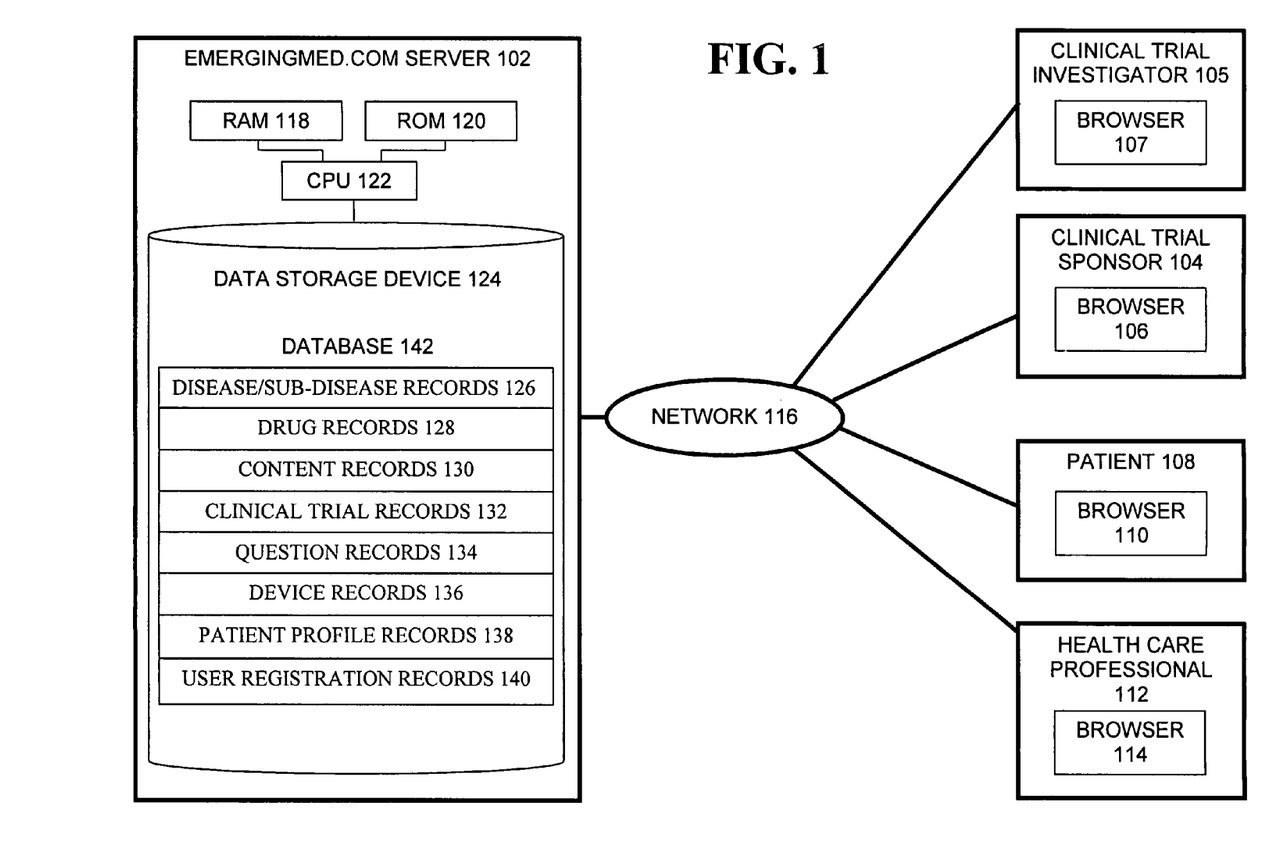
FIG. 1 depicts a block diagram illustrating the system of the present invention.

FIG. 1 depicts a block diagram illustrating the system of the present invention. An EmergingMed.com server 102 is connected to a network 116. Network 116 can be any network connecting computers such as the Internet. Sponsors of clinical trials utilize a clinical trial sponsor terminal 104 to access EmergingMed.com server 102 and to communicate with other terminals connected to network 116. Clinical trial sponsor terminal 104 is running browser program 106 which allows terminal to access remote servers and communicate with other terminals via network 116.

Patients and other individuals can access EmergingMed.com server 102 by using patient terminal 108 which is running browser program 110. Healthcare professionals can access EmergingMed.com server 102 by using health care professional terminal 112 running browser program 114. Clinical trial investigators can access EmergingMed.com server 102 by using clinical trial investigator terminal 105. Other individuals can similarly access EmergingMed.com server 102 by using any terminal connected to network 116.

EmergingMed.com server 102 includes a CPU 122 which is running a program which operates the method of the present invention. CPU 122 accesses RAM 118, ROM 120, and data storage device 124. Data storage device 124 can be any magnetic or optical media, or any other medium for storing electronic data. As will be understood by one of skill in the art, EmergingMed.com server 102 can comprise multiple servers working together, and data storage device 124 can similarly comprise multiple storage devices.

Data storage device 124 contains a database 142. Database 142 contains information organized into records. Some exemplary records are shown in FIG. 1. Disease/sub-disease records 126 contain information related to specific diseases. These records are organized both by disease and sub-disease. An example of a disease is "cancer" and an example of a sub-disease is "skin cancer." Disease/sub-disease records 126 contain information about the disease such as description of the disease, symptoms, treatment, history, and other pertinent information. Each disease/sub-disease record 126 also includes links to other related records in database 142 such as drug records 128 (e.g. drugs used to treat the disease), content records 130, clinical trial site records 132, question records 134, and device records 136. The links between records are described in more detail with respect to FIG. 3.

Drug records 128 contain information about various drugs. Such information includes the purpose of the drug, compound name, generic name, brand names, instructions for taking the drug, warnings, side effects, and any other pertinent drug information. Each drug record 128 contains links to other records in database 142.

Content records 130 contain various kinds of content such as newspaper and journal articles, research reports, frequently asked questions, standard therapies, alternate medicine, case studies, and various other types of medical information that would be of interest to someone seeking information about diseases and treatments. Content records 130 contain links to other records in database 124.

Clinical trial site records 132 contain information pertaining to various clinical trial sites. Clinical trials are performed for various reasons such as to test the efficacy of a new drug, a new medical device, or a new therapy. Clinical trials are often performed prior to obtaining FDA approval. One clinical trial may take place at multiple clinical trial sites. Each clinical trial site preferably has its own record in clinical trial site records 132. A clinical trial is conducted by an investigator on behalf of a sponsor at a clinical trial site.

Clinical trial site records 132 contain information about the clinical trial site such as the sponsor's name and information, investigator's name and information, location, number of patients admitted, number of patients allowed, open or closed status, drug or device being tested, names of staff, duration of trial, phases of the trial, purpose of the trial, trial methodology, and any other information relevant to the clinical trial being performed. Clinical trial site records 132 contain links to other records in database 142.

Question records 134 contain questions that are asked to users who are seeking to join clinical trials. As explained in detail with respect to FIG. 2, patients who are seeking to join clinical trials are asked a series of questions about their disease, their prior treatment, and their medical history. The answers to these questions are used to build a patient profile. If the answers to these question match the acceptance criteria for a specific clinical trial, then the patient becomes eligible to apply for that clinical trial. Question records 134 contain links to other records in database 142.

Device records 136 contain information about various medical devices such as the device manufacturer name, the diseases and conditions treated, instructions for using the device, warnings, and other pertinent device information. Device records 136 contain links to other records in database 142.

User registration records 140 contain user information about the various users authorized to access EmergingMed.com server 102. User registration records 140 contain information such as user name, user ID number, login name, password, access privileges, customized user preferences, mail accounts, links to patient profiles, and any other similar user information.

Patient profile records 138 contain various types of medical information about patients including their gender, age, medical histories, diseases, symptoms, and any other relevant medical information. Patient profile records are created by asking the patient a series of questions. The responses are used to build the patient's profile. The responses can be entered by a health care professional or by the patients themselves.

In a preferred embodiment of the invention, patient profile records 138 do not contain the user's name, but instead only contain the user's ID number. In other words, the patient's medical information is kept separate from the patient's identifying information. This maintains the user's medical privacy and anonymity. As will be described in more detail with respect to FIG. 2, every patient is assigned a user ID number. The user's name and identifying information is stored in the user's registration record 140 along with the user's ID number. The patient's medical information is stored in a patient profile record 138 along with the patient's user ID number. In this way, the patient's profile record 138 can be sent to a third party without revealing the patient's identity to the third party. In this way, EmergingMed.com has access to the patient's identifying information, but third parties do not. Additional records can be added to database 142 for various other purposes. Also, the organization of the records shown in FIG. 1 is by example only, and different organizations and groupings of records is possible.

Figure 2:
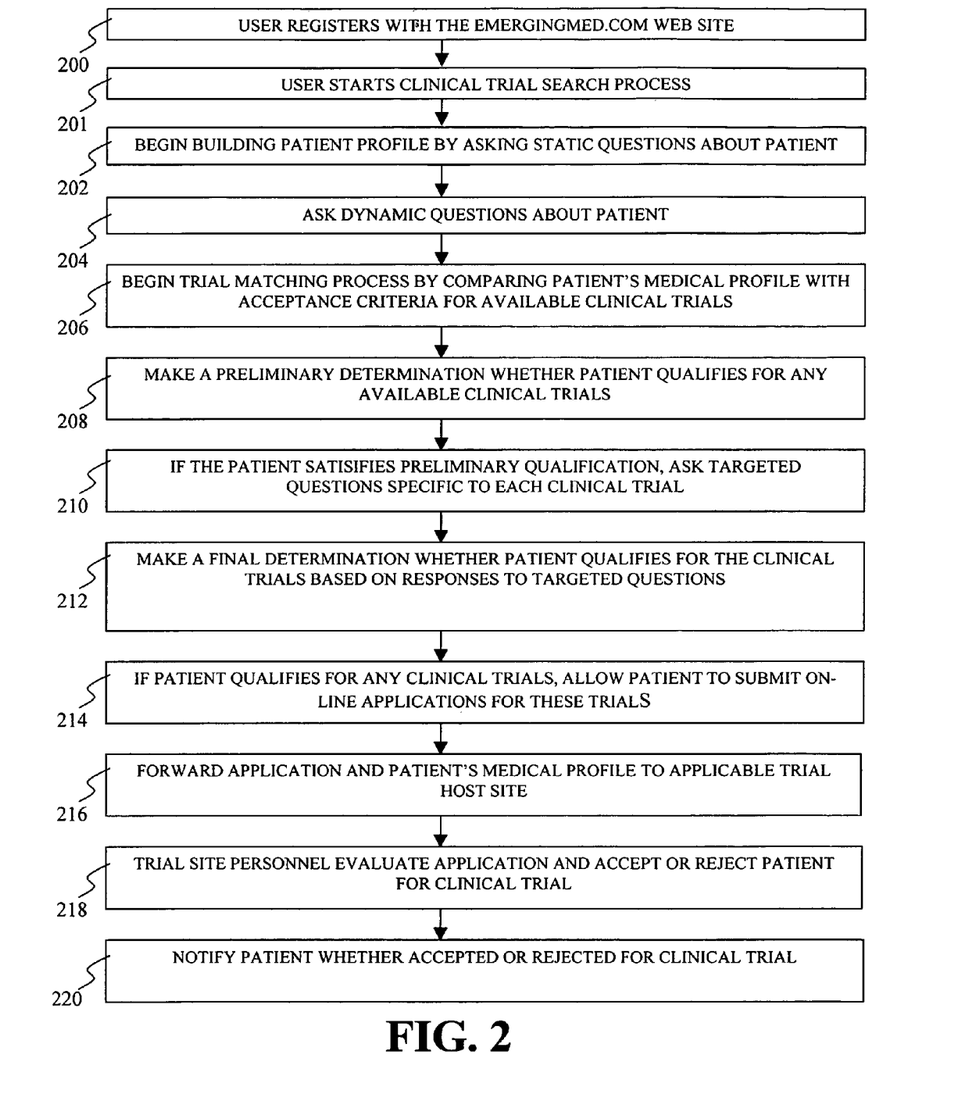
FIG. 2 depicts a flowchart illustrating a method of matching a patient with available clinical trial sites and prequalifying patients for clinical trials.

FIG. 2 depicts a flowchart illustrating a method of matching a patient with available clinical trials. In step 200, a user registers with the EmergingMed.com web site. The user could be a patient, a health care professional such as a doctor, a representative from a clinical trial sponsor, an investigator, a representative from a health care facility or clinical trial site, or any other individual or entity involved in the clinical trial process.

When a user registers, the user selects a user name and a password. The user can also submit an e-mail address. This information is stored in a user registration record 140. The user is also assigned a user ID number. This user ID number is attached to the user's profile records/medical information in order to keep the user-patient's identity anonymous.

In step 201, a user interested in searching for available clinical trials accesses the EmergingMed.com web site by entering an appropriate URL such as http://www.emergingmed.com. The user then clicks on a link or a series of links that directs the user to the clinical trial search process.

One type of user that might be interested in searching for an available clinical trial is simply a patient or a relative or friend of a patient. The user could also be a health care professional such as the patient's doctor.

The first step in finding appropriate clinical trials is creating a patient profile for the patient. The patient profile will contain the patient's medical information and any of the patient's characteristics that would be useful in determining whether a patient was suitable for a particular clinical trial.

The patient profile is created by asking the user a series of questions. In step 202, the user is asked a series of "static" questions. Static questions are a series of pre-defined questions that are asked about every patient. Examples of static questions include the patient's gender, age, height, weight, name of disease, name of sub-disease, smoker (yes/no), willing to travel (yes/no), and any other pertinent medical or patient information. The user can select a disease and sub-disease from a set of menus. For example, the user could select the disease "cancer" and the sub-disease "skin cancer." Optionally, the user can select the types of trials for which he or she is interested. For example, the user can select the trial sponsor type, trial modality, trial type of study, and drug or compound name.

Note that the "user" is not necessarily the "patient." As an example, a patient's doctor could be the "user" who accesses EmergingMed.com. The patient's doctor then enters information about the patient to build the patient profile. Using this example, the patient's doctor is doing the searching for clinical trials on behalf of the patient. In step 204, the user is asked a series of "dynamic" questions about the patient. The dynamic questions are questions which are selected based on the user's previous answers to other questions. Many of the dynamic questions will be questions which are unique to the specific selected disease and sub-disease.

When the user is presented with questions, the user is also presented with a group of answer options. The user can click on one or more of the answer options to respond to the question (some questions only allow one answer option to be selected, whereas other questions allow multiple answer options to be selected).

Preferably the questions asked to the patient, and the answer options provided to the patient, are such that a computer software program can evaluate and score the answers to the questions, rather than having a human being evaluate the answers. For example, one type of question that is easy to evaluate and/or score by a computer program is a question that allows the patient to choose one or more answers from a set of discrete multiple-choice answers. This type of question is very easy for a computer to evaluate and/or assign a score. As another example, if the patient is required to enter a numerical number, such as enter the patient's blood pressure, height or weight, this is also very easy for a computer to evaluate and/or assign a score. However, if the patient were asked "Please describe your pain" and then the patient were allowed to enter a text message, then a computer would have a difficult time evaluating this answer. A human would have to read the answer and evaluate the answer.

Some example questions are presented as follows:
Please select any or all prior cancer treatments (followed by a list of treatments, patients can click on any treatments they have had).
How many times did you have surgery?
Please select all dates that correspond to your surgeries (followed by a list of dates that the patient can click on).
Select all surgical procedures performed to date.
Was your surgery followed by (followed by a list of choices)?.
Was your surgery proceeded by (followed by a list of choices)?
How many chemotherapy regimes have you received?
Please select all dates that correspond to your chemotreatment.
Which organs are affected by malignancies at this time?
What is the stage of cancer at the time of diagnosis?

The user can be asked different levels of dynamic questions. For example, depending on the user's answer to a particular question, the user can be asked a follow-up dynamic question. If the user answers this question in a certain way, the user can be asked another follow-up question to the follow-up question. In this way the user is automatically steered through the process of building a patient profile. As an example, if the user selects "Lung Cancer" as a disease, the user could be asked "Are you a smoker?" If the user selects "YES", then the user could be asked: "How many cigarettes a day do you smoke?." If the user selects "More than five", then the user could be asked "How many years have you smoked?" In this way the user is steered through the process of building a patient profile.

Once all the questions have been answered, static and dynamic, a patient profile is created. The patient may save the profile for later use. The patient profiles is stored in patient profile records 138 in database 142. In step 206, EmergingMed.com server 102 begins a process of determining whether the patient's profile matches any available ongoing clinical trials by comparing the patient's profile with acceptance criteria for available on-going clinical trials.

As explained previously, the answers requested from the users are suitable for a computer software program to score and evaluate. Thus, a computer program process can automatically determine whether the patient prequalifies. This eliminates the need to have people review the patient's profile to determine prequalification.

In step 208, the system makes a preliminary determination of whether the patient qualifies for any available on-going clinical trials. The trial matching is preferably done at the trial site level, not the trial level. For example, a drug manufacturer may be sponsoring a clinical trial for a new drug at many trial sites around the country. The patient's profile is compared to each individual trial site to determine whether the patient prequalifies for that individual trial site. Different trial sites for the same trial could have different acceptance criteria. For example, a particular trial site may be limited to patients living within twenty miles of the trial site.

One method that can be used to determine whether a patient prequalifies for a particular trial site, is that the patient prequalifies for a trial site only if the patient meets all of the acceptance criteria for that specific trial. For example, a trial site could require that a patient must be female between the ages of 30-40 who has breast cancer, does not drink alcohol, and lives within twenty five miles of New York City. If the patient meets all of these criteria, then the patient will be prequalified for that trial site.

An alternative method of prequalifying patients is to calculate a score based on the answers given by the patient. For example, the score could simply be the number of criteria met by the patient. More complicated algorithms could also be used to generate a score. For example, the score could include the patient's blood pressure divided by two, plus three times the patient's age, and so on. The patient would then qualify only if the score exceeded or was less than a predetermined threshold or within certain predetermined threshold limits. There can also exist a combination of a score threshhold, and criteria which must be satisfied in order to qualify. For example, in order to qualify for a particular trial site, patients could be required to be female, over 35, and have a score over 253 where the score is based on a number of other factors.

Some examples of acceptance criteria that can be used include: the patient must be within a certain age range, must be female, must live within a certain geographic region, must have skin cancer, must have not had previous surgery, must have been diagnosed with cancer within the last six months, cancer must not have spread to other body organs, etc.

As mentioned previously, the users are required to enter answers to patient profile questions in a format that is suitable for evaluation by a computer program process. Optionally, the user could be provided with a combination of questions: some questions requiring answers in numerical or multiple choice format, and some questions requiring a text description to be entered by the user. The former type of questions are used to perform the automatic prequalification of the patient. The descriptive answers entered by the patient could later be sent to the clinical trial site for evaluation by clinical trial site personnel.

Acceptance criteria for clinical trial sites are typically provided by the clinical trial sponsors. Alternatively, the acceptance criteria could also be provided by clinical trial site investigators. One method of providing acceptance criteria to EmerginMed.com is to have the clinical trial sponsor or clinical trial investigator provide acceptance criteria to server administration personnel at EmergingMed.com. The acceptance criteria could be sent to EmergingMed.com by regular mail, by fax, by e-mail, over the telephone or any other communication method. The EmergingMed.com server administration personnel then program EmergingMed.com server 102 to use the acceptance criteria to qualify patients for that particular clinical trial.

An alternative method is to allow clinical trial sponsors and/or clinical trial investigators to be provided with access privileges to the EmergingMed.com server 102. The sponsors or investigators could then access the EmergingMed.com web site via network 116. A link or group of links would direct the sponsors or investigators to a web page that allows the sponsors/investigators to automatically enter acceptance criteria. Database 142 is scaleable and updateable by EmergingMed.com 102 personnel. In some instances, other parties such as clinical trial sponsors and investigators can be given access privileges (as described above) to enter data such as acceptance criteria, questions, answers, etc. The static and dynamic questions asked to patients to build their patient profile can be updated and/or supplemented frequently to reflect new medical developments, trial site selection criteria, new clinical trials, amendments to clinical trial protocols, and other developments.

Users can also be informed of the number of trials for their disease for which the patient does do not qualify, or how many trials are currently closed, or potentially if there is a waiting list available for which the patients can sign up. For example, the user could be informed that for skin cancer there are currently ten trials available and the patient qualifies for three of those ten.

After the system has made a preliminary determination of whether the patient prequalifies for any clinical trials, in step 210 the system can provide targeted questions specific to each clinical trial for which the patient has preliminarily qualified. Once the system has received responses to these targeted questions, then in step 212 the system makes a final determination as to whether the patient prequalifies for any of the clinical trials based on the user's responses to the targeted questions.

In step 214, if the patient prequalifies for any clinical trials, the patient is then provided with an application to fill out. The patient is allowed to submit an-line application for each trial site for which he or she qualifies. The patient's applications and medical profile are submitted online to EmergingMed.com server 102. Alternatively, the patients could submit their applications and profiles by other methods such as by mail or by facsimile.

In step 216, the patient's applications are forwarded along with the patient's medical profile to the appropriate trial site investigators or designated staff. The applications can be submitted to the trial site online, or alternatively, by other methods such as mail or facsimile. As described previously, the patient's medical profile and application preferably does not contain the patient's name, social security, and other identifying information. The patient's medical profile and application only include a patient ID number. In this way, the patient's privacy is protected in accordance with government regulated confidentiality standards. A copy of the patient's application/profile, a summary of the patient's application/profile, or a notification could optionally be sent to the trial sponsor in addition to the trial site.

As an alternative to submitting applications to the trial sites via EmergingMed.com web server 102, the applications could alternatively be submitted directly by the patient to the trial site investigators or staff. However, it may be preferable to send all information to the trial site via EmergingMed.com server 102 in order to maintain the privacy of patients' identity.

Another method of sending the patient's application and profile to the trial site investigator is as follows. The trial site investigator or contact person has a designated "mailbox" in a message center on EmergingMed.com server 102. The patient therefore sends a message to the investigator/contact person containing the application and profile. This message is then stored on the EmergingMed.com server 102 and can be retrieved by the investigator/contact person.

In step 220, the patient is notified whether he or she has been successfully prescreened or rejected for the clinical trial site which the patient has applied. The patient can be telephoned or e-mailed or contacted by other means. Alternatively, the patient can access the EmergingMed.com web site and check his or her status. If the patient has successfully prequalified for a clinical trial site, the patient can be provided with contact information at the trial site. The patient can then contact the appropriate person at the trial site (either through a message left in the EmergingMed.com server 102 message center or through other contact means) to inquire about enrolling in the clinical trial site or to seek further information. The clinical trial site may then require that the patient undergo further medical testing or answer further questions before the patient is enrolled in a clinical trial.

Another feature provided by EmergingMed.com server 102 is to allow users to search and obtain medical information about diseases, drugs, medical devices, treatments, clinical trials, and any other pertinent information. In this way, patients and health care professionals can educate themselves about a disease, standard or experimental treatments, and ongoing clinical trials before deciding whether to participate in any clinical trials. This process is enhanced by providing many links between the various records shown in database 142 in FIG. 1.

The method just described and shown in FIG. 2 is a method of matching patients with clinical trial sites. The system of the present invention can also perform other types of matching such as:

patient to patient matching
  trial sponsor to investigator matching
  investigator to trial site matching Patient to patient matching involves matching one patient with another patient based on their patient profiles. For example, a patient with a particular disease could be matched with other patients with a similar disease. This allows the patients to automatically form a support group. A patient could be provided e-mail addresses of other matching patients so that they can be contacted. Each patient could be provided with an anonymous e-mail name so that the patient privacy can be protected. Alternatively, messages could be addressed to a user ID number.

Trial sponsor to investigator matching involves matching a clinical trial sponsor with an investigator suitable for conducting the trial. For example, a drug company might be interested in finding a researcher with 20 years of experience researching breast cancer treatment in the Milwaukee area. Investigator to trial site matching involves matching investigators with trial sites that are looking for investigators with particular qualifications. What all of these methods share in common is that the EmergingMed.com server 102 finds matches between matching parties and performs an initial layer of prequalification or prescreening before bringing the parties together.

FIG. 3 depicts a block diagram illustrating some exemplary links between various records in data storage device 120. These links allow a user to navigate the web site and efficiently find medical information relevant to their particular medical condition. The user can also search for relevant information by entering keyword queries. For example, a user searching for particular information about a particular disease would enter the name of a disease and sub-disease such as "cancer/skin cancer." This would retrieve disease/sub-disease record 300 for skin cancer. Disease/sub-disease record 300 would contain information about skin cancer which would be provided to the user. When the user accesses disease/sub-disease record 300, the user is provided with all of the information contained in record 300 as well as links to records 302, 304, 305, and 306. The user can then click on one of these links to access the linked record.

Figure 3A:
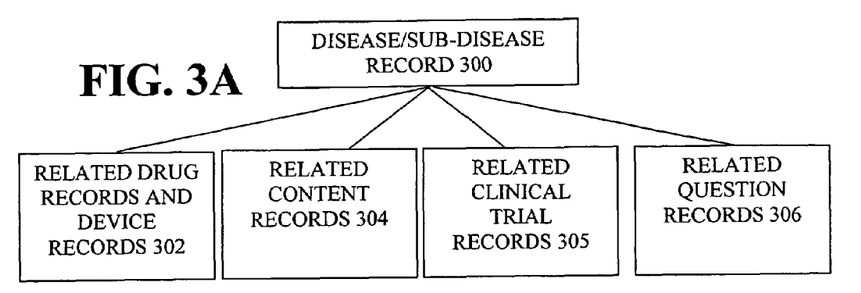
FIGS. 3A-3D depict block diagrams illustrating some exemplary links between various records in data storage device 120.

Disease/sub-disease record 300 contains links to related drug/device records 302. These drug/device records are associated with drugs and medical devices used to treat the disease/sub-disease associated with disease/sub-disease record 300. The drug/device records 302 contain information about their associated drug or device such as instructions for taking a drug or using a medical device, warnings, side effects, and similar information.

Disease/sub-disease record 300 also contains links to content records 304. Content records 304 contain additional information about the disease/sub-disease such as related news and journal articles, standard therapies, therapies in development, case studies, alternative treatments, and frequently asked questions.

Disease/sub-disease records 300 also contain links to clinical trial records 304. Clinical trial records 304 contain information about various clinical trials which address the specific disease/sub-disease such as the clinical trial sponsor type, trial site locations, acceptance criteria, number of people admitted, and so on. Disease/sub-disease records 300 also contain links to related question records 306. These are questions that are asked to users who are seeking to qualify for clinical trials. These questions are asked in step 204 in FIG. 2.

Figure 3B:
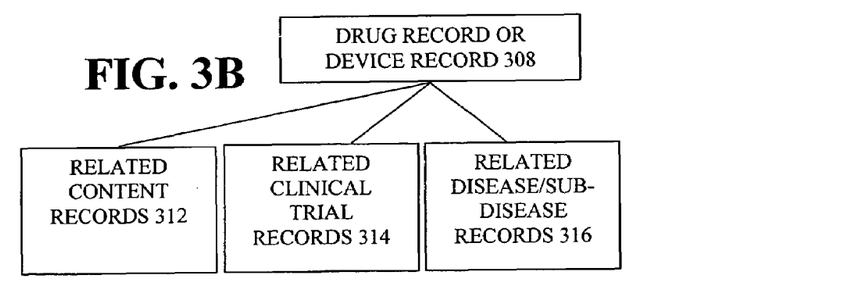

FIG. 3B shows another set of links emanating from drug or device record 308. A user can access a drug or device record 308 to find out information about that drug or device. The user will be presented with links to related content records 312 which provide content related to that drug or device. The user will also be presented with links to related clinical trial records 314. The user will also be presented with links to related disease/sub-diseases records 316.

Figure 3C:
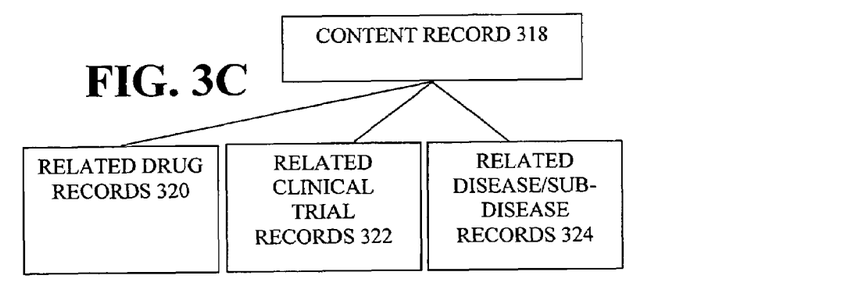

FIG. 3C shows another set of links emanating from content record 318. Content record 318 could be a news or journal article, or some other piece of information. Content record 318 contains links to related drug records 320, related clinical trial records 322, and related disease/sub-disease records 324.

Figure 3D:
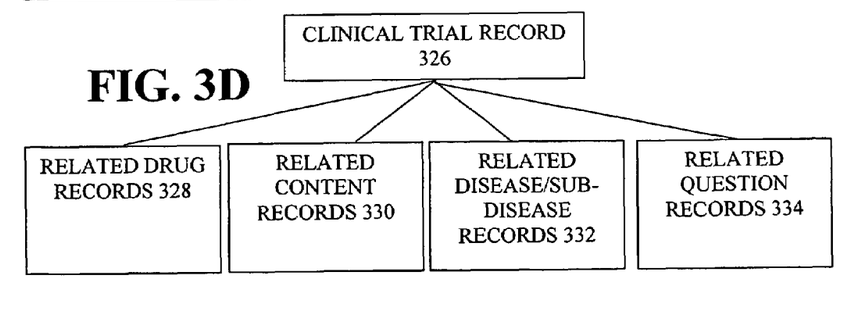

FIG. 3D depicts another set of links emanating from clinical trial record 326. Clinical trial record 326 contains links to related drug records 328, related content records 330, and related disease/subdisease records 332. Clinical trial record 326 also contains links to related question records 334. These questions are asked to users in step 210 of FIG. 2 to determine if they qualify for the specific clinical trial.

Another method of the present invention is to allow third party web sites to perform the trial matching and prequalification of the present invention. For example, suppose a drug company has its own web site www.DrugCompany.com. DrugCompany.com has a contract with EmergingMed.com to allow users of DrugCompany.com to perform trial matching and prequalification.

When a user visits DrugCompany.com, the user is provided with a link or group of links which allows the user to search for clinical trials. There are various methods that can be used to allow DrugCompany.com to interface with EmergingMed.com server 102. In a first method, the DrugCompany.com server relays all of the data entered by the user to the EmergingMed.com server 102. The DrugCompany.com server then receives the data sent by EmergingMed.com server 102 and forwards it to the patient. DrugCompany.com thus acts as an intermediary or proxy server for the EmergingMed.com server. Another method is to provide DrugCompany.com with all of the software necessary to ask the patient's questions to build a patient profile. DrugCompany.com could then relay the information to EmergingMed.com server 102. EmergingMed.com server 102 could search database 124 and forward the results to DrugCompany.com. A variety of other well known methods could be used to access EmergingMed.com server 102 via DrugCompany.com.

A patient who performs trial matching and prequalification at DrugCompany.com can also be limited to searching only subsets of the total available clinical trial sites. For example, the users at DrugCompany.com could be limited to only searching for clinical trials sponsored by DrugCompany.com.

Although the present invention has been described in terms of various embodiments, it is not intended that the invention be limited to these embodiments. Modification within the spirit of the invention will be apparent to those skilled in the art. The scope of the present invention is defined by the claims that follow.

The invention claimed is:

1. A method for matching patients with clinical trials, comprising:
    receiving acceptance criteria for clinical trials and a series of questions targeted to at least one specific clinical trial at a server, wherein the acceptance criteria for clinical trials and the series of questions targeted to at least one specific clinical trial are provided over the Internet by a system of a clinical trial sponsor or investigator;
    receiving patient profile information for a patient at the server, the patient profile information submitted over the Internet by a user at a user terminal;
    comparing the patient profile information with the acceptance criteria for clinical trials stored in a database, the comparison performed by the server; and
    automatically, determining that the patient prequalifies for any of the clinical trials based on the comparison of the patient profile information with the acceptance criteria;
    notifying the user that the patient has prequalified for at least one specific clinical trial when the patient prequalifies for any of the clinical trials;
    presenting to the user the series of questions targeted to the at least one specific clinical trial after determining that the patient prequalifies for any of the clinical trials, wherein the series of questions are provided by the server to the user terminal over the Internet;
    determining that the patient prequalifies for the at least one specific clinical trial based on responses to the targeted questions;
    storing the responses to the targeted questions;
    providing the user with an application for the user to request that the patient be a participant in the specific clinical trial at a clinical trial site for the specific clinical trial when the patient prequalifies for the at least one specific clinical trial, wherein the application is provided by the server to the user terminal over the Internet; and
    providing the contact information for the clinical trial site when the completed application is accepted.

2. The method of claim 1, further including providing the user with instructions for enrolling the patient in the specific clinical trial.

3. The method of claim 1, wherein receiving patient profile information further includes asking the user a plurality of questions; and creating a patient profile based on the responses to the plurality of questions.

4. The method of claim 3, wherein the step of asking the user a plurality of questions includes:
    asking one or more static questions;
    asking one or more dynamic questions which are selected based on responses to other static and dynamic questions; and
    creating the patient profile based on the responses to the static and dynamic questions.

5. The method of claim 4, wherein static questions, dynamic questions, and targeted questions are provided with a plurality of answer options, and the user may select one or more answer options in order to answer the questions.

6. The method of claim 5, wherein an answer is submitted in a specified format, the specified format being suitable for evaluation by a computer program process.

7. The method of claim 6, further including:
    updating the static questions, dynamic questions, or answer options.

8. The method of claim 1, wherein the completed application is submitted to the server.

9. The method of claim 8, wherein the completed application is forwarded to the clinical trial site.

10. The method of claim 9, wherein the patient profile is forwarded to the clinical trial site with the completed application.

11. The method of claim 10, wherein the completed application and patient profile forwarded to the clinical trial site includes a patient ID number, but does not include the patient's name to protect the privacy of the patient.

12. The method of claim 11, further including:
    notifying the clinical trial sponsor when the completed application is submitted to the clinical trial site.

13. The method of claim 1, wherein a search engine is provided that allows a search for medical information before selecting a clinical trial.

14. The method of claim 1, wherein the acceptance criteria includes geographic location.

15. A system for matching patients with clinical trials, comprising:
    a server connected to the Internet;
    a data storage device included in the server;
    a database located in the data storage device, the database storing patient profile information for a patient and acceptance criteria for a plurality of clinical trials
    a system of a clinical trial sponsor or investigator for providing the acceptance criteria for clinical trials and a series of questions targeted to at least one specific clinical trial to the server over the Internet; and
    a user terminal for providing the patient profile information for the patient to the server over the Internet;
    the server comparing the patient profile information with the acceptance criteria for the clinical trials stored in the database; automatically, determining that the patient prequalifies for any of the clinical trials based on the comparison of the patient profile information with the acceptance criteria; notifying the user that the patient has prequalified for at least one specific clinical trial when the patient prequalifies for any of the clinical trial; presenting to the user the series of questions targeted to the at least one specific clinical trial after determining that the patient prequalifies for any of the clinical trials, wherein the series of questions are provided by the server to the user terminal over the Internet; determining that the patient prequalifies for the at least one specific clinical trial based on responses to the targeted questions, storing the responses to the targeted questions; providing the user with an application for the user to request that the patient be a participant in the specific clinical trial at a clinical trial site for the specific clinical trial when the user prequalifies for the at least one specific clinical trial, wherein the application is provided by the server to the user terminal over the Internet, and providing the contact information for the clinical trial site when the completed application is accepted.

16. The system of claim 15, wherein the database contains at least one of:
   a) diseasehub-disease records;
   b) drug records;
   c) content records;
   d) clinical trial records;
   e) question records;
   f) device records;
   g) patient profile records;
   g) user registration records; and
   g) trial site records.

17. The system of claim 16, wherein a record in the database contains links to other related records.

18. The system of claim 16, wherein the server transmits a plurality of questions over the Internet, the server also transmits a plurality of answer choices for each question, the server receives responses, and the server builds a patient profile based on the responses.

19. The system of claim 15, wherein the server retrieves a disease/sub-disease record corresponding to a received disease/sub-disease, the disease/-sub-disease record containing links to question records, the server retrieving the question records to access questions.

20. The system of claim 15, wherein the completed application is submitted to the server.

21. The system of claim 20, further comprising the server forwarding to the completed application to the clinical trial site.

22. The system of claim 21, further comprising the server forwarding the registration information to the clinical trial site with the completed application.

23. The system of claim 22, wherein the completed application and registration information forwarded to the clinical trial site includes a patient ID number, but does not include the patient's name to protect the privacy of the patient.

24. The system of claim 23, further including:
   the server notifying the clinical study sponsor when the completed application is submitted to the clinical trial site.

25. The system of claim 15 further comprising,
   providing a search engine that allows a search for medical information before selecting a clinical study.

26. Computer executable software code stored on a computer readable medium, performing a method for matching patients with clinical trials, comprising:
   receiving acceptance criteria for clinical trials and a series of questions targeted to at least one specific clinical trial at a server, wherein the acceptance criteria for clinical trials and the series of questions targeted to at least one specific clinical trial are provided over the Internet by a system of a clinical trial sponsor or investigator;
   receiving patient profile information for a patient at the server, the patient profile information submitted over the Internet by a user at a user terminal;
   comparing the patient profile information with the acceptance criteria for clinical trials stored in a database, the comparison performed by the server; and
   automatically, determining that the patient prequalifies for any of the clinical trials based on the comparison of the patient profile information with the acceptance criteria;
   notifying the user that the patient has prequalified for at least one specific clinical trial when the patient prequalifies for any of the clinical trials;
   presenting to the user the series of questions targeted to the at least one specific clinical trial after determining that the patient prequalifies for any of the clinical trials, wherein the series of questions are provided by the server to the user terminal over the Internet;
   determining that the patient prequalifies for the at least one specific clinical trial based on responses to the targeted questions;
   storing the responses to the targeted questions;
   providing the user with an application for the user to request that the patient be a participant in the specific clinical trial at a clinical trial site for the specific clinical trial when the patient prequalifies for the at least one specific clinical trial, wherein the application is provided by the server to the user terminal over the Internet; and
   providing the contact information for the clinical trial site when the completed application is accepted.

27. The computer executable software code of claim 26, wherein the completed application is submitted to the server.

28. The computer executable software code of claim 27, further comprising the forwarding to the completed application to the clinical trial site.

29. The computer executable software code of claim 28, further comprising the forwarding the registration information to the clinical trial site with the application.

30. The computer executable software code of claim 26, wherein the completed application and registration information forwarded to the clinical trial site includes a patient ID number, but does not include the patient's name to protect the privacy of the patient.

31. The computer executable software code of claim 30, further including: the server notifying the clinical study sponsor when the completed application is submitted to the clinical trial site.

32. The computer executable software code of claim 26, further comprising providing a search engine that allows a search for medical information before selecting a clinical study.

* * * * *